(12) United States Patent
Harbeck et al.

(10) Patent No.: US 7,772,011 B2
(45) Date of Patent: Aug. 10, 2010

(54) METHOD AND KIT FOR DETECTION OF AUTOIMMUNE CHRONIC URTICARIA

(76) Inventors: Ronald Joseph Harbeck, 1890 S. Xenia Ct., Denver, CO (US) 80231; Karen Mary Andrews, 10391 Galatia Ct., Longmont, CO (US) 80503; Donald MacGlashan, Jr., 221 Rickswood Rd., Lutherville Timonium, MD (US) 21093-3029

(*) Notice: Subject to any disclaimer, the term of this patent is extended or adjusted under 35 U.S.C. 154(b) by 359 days.

(21) Appl. No.: 11/387,089

(22) Filed: Mar. 21, 2006

(65) Prior Publication Data

US 2007/0048802 A1    Mar. 1, 2007

Related U.S. Application Data

(60) Provisional application No. 60/664,090, filed on Mar. 21, 2005.

(51) Int. Cl.
*G01N 33/564* (2006.01)
*G01N 33/00* (2006.01)

(52) U.S. Cl. ............... 436/506; 435/3; 435/7.2; 435/7.24; 435/287.2; 435/372; 435/973; 436/507; 436/513; 436/35; 436/63; 436/811

(58) Field of Classification Search .......... 435/2, 435/3, 6, 7.2, 7.24, 372, 386, 387.1, 973, 435/287.2; 436/506, 507, 513, 517, 548, 436/10, 35, 52, 63, 172, 811, 73, 82.05
See application file for complete search history.

(56) References Cited

U.S. PATENT DOCUMENTS

2005/0003461 A1    1/2005 Buehring

FOREIGN PATENT DOCUMENTS

| WO | WO 03025566 | 3/2003 |
|---|---|---|
| WO | WO 03048779 | 6/2003 |
| WO | WO 2005007695 | 1/2005 |

OTHER PUBLICATIONS

Ebo et al., In vitro allergy diagnosis: should we follow the flow?, Clin. Exp. Allergy 34: 332-339 (2004).*
Vasagar et al., Evidence of In Vivo Basophil Activation in Chronic Idiopathic Urticaria, J. Allergy Clin. Immunol. 113 (2): Abstract S257, No. 928 (2004)).*

(Continued)

*Primary Examiner*—Gailene R Gabel
(74) *Attorney, Agent, or Firm*—Sheridan Ross P.C.

(57) ABSTRACT

Disclosed is a rapid, non-invasive and highly specific and sensitive diagnostic assay for the identification of individuals with autoimmune chronic urticaria, which makes use of CD203c, and in some embodiments, additional proteins, as a marker for the disease. Test kits for diagnosis of an individual suspected of having autoimmune chronic urticaria are also disclosed. Also disclosed are a method of identifying compounds useful for treating autoimmune chronic urticaria and a method of treating autoimmune chronic urticaria.

13 Claims, 5 Drawing Sheets

OTHER PUBLICATIONS

Gyimesi et al., Basophil CD63 expression assay on highly sensitized ectopic donor leucocytes—a useful method in chronic autoimmune urticaria, British Journal of Dermatology 151: 388-396 (2004).*

Wedi et al., Chronic Urticaria serum induces histamine release, leukotriene production, and basophil CD63 surface expression-Inhibitory effects of anti-inflammatory drugs, J. Allergy Clin. Immunol. 105: 552-560 (2000).*

Boumiza et al., Marked improvement of the basophil activation test by CD203c instead of CD63, Clin. Exp. Allergy 33:255-265 (2003)).*

Hauswirth et al., Recombinant allergens promote expression of CD203c on basophils in sensitized individuals, J. Allergy Clin. Immunol 110: 102-109 (2002).*

Boumiza et al., "Marked Improvement of the basophil activation test vy detecting CD203c instead of CD63", Clinical and Experimental Allergy : Journal of the British Society for Allergy and Clinical Immunology, vol. 33, pp. 259-265, 2003.

Bühring, et al., "The basophil activation marker defined by antibody 97A6 is identical to the ectonucleotide pyrophosphatase/phosphodiesterase 3", Blood, vol. 97, No. 10, pp. 3303-3305, May 15, 2001.

Bühring, et al., "The Basophil-Specific Ectoenzyme E-NPP3 (CD203c) as a Marker for Cell Activation and Allergy Diagnosis", International Archives of Allergy and Immunology, vol. 133, pp. 317-329, 2004.

Ebo, et al., "Regarding Boumiza r., Monneret G., Forrissier M-F, et al. Marked Improvement of the basophil activation test vy detecting CD203c instead of CD63," Clinical and Experimental Allergy : Journal of the British Society for Allergy and Clinical Immunology, vol. 33, pp. 849-853, 2003.

Ebo, et al., "In vitro allergy diagnosis: should we follow the flow?", Clinical and Experimental Allergy : Journal of the British Society for Allergy and Clinical Immunology, vol. 34, pp. 332-339, 2004.

Gyimesi, et al., "Clinical and Laboratory Investigation; Basophil CD63 expression assay on highly sensitized atopic donor leucocytes—a useful method in chronic autoimmune urticaria", British Journal of Dermatology, vol. 151, pp. 388-396, 2004.

Hauswirth, et al., "Recombinant allergens promote expression of CD203c on basophils in sensitized individuals", The Journal of Allergy and Clinical Immunology, vol. 110, No. 1, pp. 102-109, Jul. 2002.

Vasagar, et al., "Evidence of In Vivo Basophil Activation in Chronic Idiopathic Urticaria", The Journal of Allergy and Clinical Immunology, vol. 113, No. 2, p. S257, 2004.

Wedi, et al., "Chronic urticaria serum induces histamine release, leukotriene production, and basophil CD63 surface expression—Inhibitory effects of anti-inflammatory drugs", Journal of Allergy and Clinical Immunology, vol. 105, No. 3, pp. 552-560, Mosby, Inc., Mar. 2000.

* cited by examiner

METHOD AND KIT FOR DETECTION OF AUTOIMMUNE CHRONIC URTICARIA

CROSS-REFERENCE TO RELATED APPLICATIONS

This application claims the benefit of priority under 35 U.S.C. §119(e) from U.S. Provisional Application No. 60/664,090, filed Mar. 21, 2005. The entire disclosure of U.S. Provisional Application No. 60/664,090 is incorporated herein by reference in its entirety.

FIELD OF THE INVENTION

This invention generally relates to a method and assay kit for the diagnosis of autoimmune chronic urticaria, and a method to treat autoimmune chronic urticaria.

BACKGROUND OF THE INVENTION

Chronic idiopathic urticaria (CU) is defined as recurrent hives occurring for at least 6 weeks. In the majority of cases, there is no identifiable trigger, despite extensive evaluation for an underlying etiology. A subset of these patients is classified as having autoimmune urticaria defined by the presence of a functional IgG antibody to the alpha-subunit of the high-affinity IgE receptor (FcεRIα) or to IgE (Kaplan, 2004). These antibodies trigger mast cell and basophil degranulation by the engagement of this receptor. Functional IgG antibody to the receptor has been identified in approximately 30-40% of patients with CU, and anti-IgE antibody has been identified in another 5-10% of patients. Non-functional antibodies to FcεRI may be found in other autoimmune conditions (Fiebiger, 1998).

Techniques to detect the autoantibody to FcεRIα include Western blot and enzyme linked immunoabsorbant assay (ELISA), which are technically time consuming and fail to identify antibodies with histamine releasing properties. Detection methods for functional antibodies include the autologous serum skin test (ASST) and basophil histamine release (BHR). The ASST involves an intradermal injection of the patient's serum into the skin with observation for a wheal and flare reaction. ASST is approximately 70% sensitive and 80% specific when compared with the basophil histamine release (BHR) assay (Aabroe, 1999).

Recently, flow cytometry has been used to identify activated basophils in both allergic disease and chronic urticaria. Upregulation of three proteins (CD63, CD203c, and CD69) on peripheral blood basophils from patients with CU has been described (Vasgar, 2003), although no correlation with autoimmune CU or histamine release was described for any of these markers.

With regard to CD63, two studies have been published demonstrating that sera of patients with CU and positive ASST induce higher expression of CD63 when compared to skin test negative chronic urticaria sera (Wedi, 2000; Gyimsi, 2004). CD63, a member of the transmembrane-4 superfamily, is a basophil and mast cell activation marker that is expressed as a result of the fusion between intracytoplasmic granules and the plasma membrane. It has been proposed that it rapidly appears on the basophil surface upon the addition of anti-IgE, allergen or IL-3 (Knol, 1991; Ebo, 2004). However, CD63 is not specific to basophils and mast cells, and can be expressed on other cells present in the peripheral blood, i.e., monocytes and platelets (Buhring, 2004).

Specifically, Wedi et al. (Wedi, 2000), who used interleukin-3 (IL-3) to activate cells in whole blood, found increased CD63 expression in 70% of ASST positive CU patients, in 45% of ASST negative CU patients, and in 35% of controls. Wedi et al. was not able to demonstrate specificity of the assay for patients with CU and the functional positive ASST, and could not correlate CD63 expression with histamine releasing activity, nor could Wedi et al. show that CD63 expression was characteristic of patients with ASST+ sera or with CU patients in general (noting the high percentage of negative controls with increased CD63 expression). Gyimesi et al (Gyimesi, 2004) attempted to improve upon the results of Wedi et al. by using donor basophils from highly sensitized atopic individuals as the test cells. Gyimesi et al. found elevated CD63 expression induced by 11/12 ASST positive sera (92%) and 3/18 (17%) of ASST negative sera. However, the use of the highly sensitized atopic donor cells appears to be a requirement for the improve sensitivity of this test.

Therefore, there remains a need in the art for a rapid, in vitro assay that is minimally invasive, and is capable of distinguishing autoimmune patients from patients with other forms of urticaria, including other forms of chronic urticaria, such as that caused by allergy (atopic patients).

SUMMARY OF THE INVENTION

One embodiment of the present invention relates to a method to diagnose autoimmune chronic urticaria. The method includes the steps of: (a) contacting isolated cells with a test biological sample from an individual being diagnosed for autoimmune chronic urticaria, wherein the isolated cells are capable of expressing CD203c and FcεRIα, and upregulate the expression of CD203c upon stimulation of the FcεRIα; and (b) detecting expression of CD203c expression on the cells. Upregulation of CD203c on the cells in the presence of the test biological sample, as compared to CD203c expression on the cells in the absence of contact with the biological sample, or as compared to CD203c expression on the cells when contacted with a negative control sample from an individual who does not have autoimmune chronic urticaria, indicates that the individual has autoimmune chronic urticaria.

In one aspect of this embodiment, the test biological sample is a fluid sample, including, but not limited to, serum or whole blood from the individual. In one aspect, the isolated cells are provided as a whole blood sample from a donor or as isolated peripheral blood cells from a donor. In one aspect, the isolated cells are provided as substantially purified cells from a donor. In another aspect, the isolated cells are provided as a cell line. In yet another aspect, the isolated cells are from a donor that does not have autoimmune chronic urticaria. In one aspect, the isolated cells have been selected as having high upregulation of CD203c expression after stimulation with a granulocyte activating agent and/or after stimulation of FcεRIα on the cells, as compared to isolated cells from a population of normal individuals that do not have autoimmune chronic urticaria. In one aspect, the cells are from a non-atopic donor. In another aspect, the isolated cells are not cultured with interleukin-3 prior to the step of contacting. In yet another aspect, the isolated cells are selected from: basophils and mast cells.

In one aspect of this embodiment of the invention, the step of detecting is performed by flow cytometry. In one aspect, the step of detecting is performed using a CD203c antibody or antigen-binding fragment thereof, including, but not limited to, a monoclonal antibody.

In one aspect of this embodiment of the invention, the cells express CD13, and the method further comprises detecting expression of CD13 by the cells. Increased expression of CD13 in the presence of the test biological sample, as compared to expression of CD13 by the cells in the absence of contact with the biological sample, or as compared to CD13 expression on the cells when contacted with a negative control sample from an individual who does not have autoimmune chronic urticaria, further indicates that the individual has autoimmune chronic urticaria.

In another aspect of this embodiment of the invention, the cells express CD164, and the method further comprises detecting expression of CD164 by the cells. Increased expression of CD164 in the presence of the test biological sample, as compared to expression of CD164 by the cells in the absence of contact with the biological sample, or as compared to CD164 expression on the cells when contacted with a negative control sample from an individual who does not have autoimmune chronic urticaria, further indicates that the individual has autoimmune chronic urticaria.

In yet another aspect of this embodiment of the invention, the cells express CD63, and the method further comprises detecting CD63 expression on the cells. Increased expression of CD63 in the presence of the test biological sample, as compared to CD63 expression on the cells in the absence of contact with the biological sample, or as compared to CD63 expression on the cells when contacted with a negative control sample from an individual who does not have autoimmune chronic urticaria, further indicates that the individual has autoimmune chronic urticaria.

In another aspect of this embodiment of the invention, the method additionally includes testing the individual by histamine release assay, wherein a positive histamine release assay further indicates that the individual has autoimmune chronic urticaria.

In yet another aspect of this embodiment of the invention, the method additionally includes testing the individual by autologous serum skin testing (ASST), wherein a positive ASST test further indicates that the individual has autoimmune chronic urticaria.

Another embodiment of the present invention relates to a kit for the diagnosis of autoimmune chronic urticaria. The kit includes: (a) isolated cells that are capable of expressing CD203c and FcεRI and that upregulate the expression of CD203c upon stimulation of FcεRI; and (b) a reagent for the detection of CD203c expression on the cells. In one aspect, the reagent for detection of CD203c expression on the cells is a CD203c antibody or antigen-binding fragment thereof, including, but not limited to, a monoclonal antibody. In one aspect, the kit also includes a reagent selected from a positive control reagent and a negative control reagent. A positive control reagent can include, but is not limited to, fMLP and/or anti-FcεRIα. A negative control reagent can include, but is not limited to, a buffer. In one aspect of this embodiment, the isolated cells are basophils.

Yet another embodiment of the present invention relates to a method to identify a compound that inhibits autoimmune chronic urticaria. The method includes the steps of: (a) contacting isolated cells that are capable of expressing CD203c and FcεRIα, and that upregulate the expression of CD203c upon stimulation of the FcεRIα, with an agent that stimulates the expression of CD203c by the cells; (b) contacting the isolated cells with a putative regulatory compound; and (c) detecting expression of CD203c expression on the cells. Prevention or inhibition of upregulation of CD203c on the cells in the presence of the putative regulatory compound, as compared to the upregulation of CD203c expression on the cells in the absence of contact with the putative regulatory compound, indicates that the putative regulatory compound is a candidate for inhibition of autoimmune chronic urticaria.

Another embodiment of the present invention relates to a method to treat autoimmune chronic urticaria, comprising administering to the individual a pharmaceutical composition that inhibits the expression or biological activity of CD203c.

BRIEF DESCRIPTION OF THE DRAWINGS OF THE INVENTION

FIGS. 1A-1C show basophil identification and expression of CD203c. FIG. 1A shows a side scatter and CD45—gating region (boxed area) contained the basophils located between the monocytes and lymphocytes. FIG. 1B shows the gated cells that were selected by high IgE and high CD203c expressing cells. FIG. 1C is a histogram of CD203c expression after addition of buffer (shaded area) and after addition of serum from a chronic urticaria patient with a positive ASST (M1 defines a region where ≦1% of the basophils express CD203c after incubation with buffer).

DETAILED DESCRIPTION OF THE INVENTION

Figures 1A, 1B, 1C:
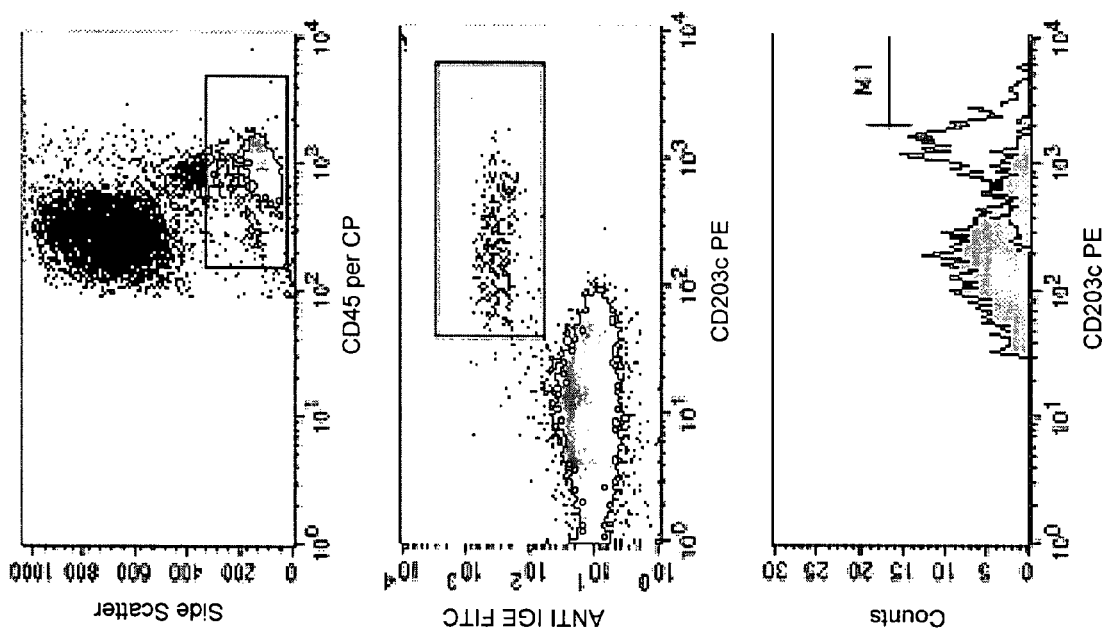

This invention generally relates to methods, reagents and kits that are useful for the detection of autoimmune chronic urticaria. The invention can be used to identify patients that have autoimmune chronic urticaria (e.g., a diagnostic, prognostic or monitoring method) and to further understand the mechanisms of chronic urticaria for the development of therapeutic strategies directed at preventing or treating this disease. In addition, the present invention generally relates to the identification of a therapeutic target for the treatment of chronic urticaria, namely, CD203c, a cell surface protein expressed primarily by basophils, and to therapeutic strategies for chronic urticaria. The present invention also relates to the use of other markers that follow the kinetics of CD203c expression in basophils as additional or alternative markers to CD203c, including, but not limited to, CD13 and CD164.

Approximately 40% of patients with chronic urticaria (CU) have antibodies to the high affinity IgE receptor (FcεRI). Patients with auto-antibodies are currently identified by histamine release assay (HR), autologous serum skin testing (ASST) and Western blot. CD203c is expressed specifically on basophils, mast cells and their CD34+ progenitor cells and is upregulated by cross-linking of FcεRI receptors. The present inventors have shown that CD203c is a highly useful marker to identify autoimmune urticaria patients with functional antibodies to the FcεRI receptor.

More particularly, the present inventors compared the effect of sera from ASST+ (autoimmune) and ASST-chronic urticaria (CU) patients on basophil CD203c expression to normal control sera, and determined whether expression of CD203c correlated with basophil histamine release (BHR). In addition, IgG depletion of sera from ASST positive individuals was performed to determine if the mechanism of CD203c upregulation is IgG-mediated.

The inventors have discovered that the sera from patients with CU upregulate basophil CD203c expression. Sera from patients with positive ASST (a known indicator of autoimmune chronic urticaria) induced significantly higher CD203c expression compared to the sera from patients with negative ASST and from normal controls. Specifically, while 20% of patient sera with negative ASSTs induced ≧5% basophil activation compared to buffer control, whereas 77% percent of patients with positive ASSTs had ≧5% basophil activation. Although sera from ASST negative patients induced higher CD203c expression than normal controls, the CD203c expression in these patients was nonetheless significantly lower than CD203c expression in ASST positive patients.

The sensitivity, specificity, positive predictive value and negative predictive value of the method or detection of CD203c as a marker for CU were calculated using the BHR assay as the gold standard to identify functional antibodies to the FcεRIα receptor, and using >5% CD203c expression as the cut-off value for a positive test. Using these criteria, CD203c expression demonstrated a sensitivity of 77%, specificity of 82%, a positive predictive value of 83% and a negative predictive value of 75%. Therefore, detection of CD203c correlates well with results from the current standard for detection of autoimmune CU.

In addition, the present inventors have demonstrated that the mechanism of expression of CD203c in CU patients is mediated by IgG. CD203c is known to be upregulated by cross-linking of FcεRIα by transport of preformed CD203c molecules to the surface (14). The decline in CD203c expression following IgG depletion of representative sera is consistent with an IgG-mediated mechanism (see Example 4), which can include an IgG antibody against the FcεRIα subunit or against IgE.

The method of the present invention is particularly useful because it can identify patients that have functional FcεRI autoantibodies in a rapid, in vitro assay that is minimally invasive and is capable of distinguishing autoimmune patients from patients with other forms of urticaria, including other forms of chronic urticaria, such as that caused by allergy (atopic patients). The method is more sensitive than diagnosis using a different marker, such as CD63, because while CD63 can be detected on a variety of cell types, CD203c is a much more specific marker of basophils and basophil degranulation, and therefore, is a much more specific marker of the cell types and mechanisms associated with the development of autoimmune chronic urticaria. Furthermore, in contrast to assays described for the detection of CD63 (Wedi, 2000; Gyimesi, 2004), the present invention does not require the use of interleukin-3 to stimulate test cells, nor the use of cells from atopic patients to increase sensitivity. Moreover, prior to the present invention, the use of CD203c as a diagnostic marker for autoimmune chronic urticaria had not been described.

CD203c belongs to the type II transmembrane protein family and is a multifunctional ecto-enzyme called ectonucleotide pyrophosphatase phophodiesterase 3 (E-NPP3) that catalyzes the cleavage of a number of molecules including deoxynucleotides and nucleotide sugars. It also contains a somatomedin B-like domain and a cell adhesive motif, but their potential functions are unknown. Among leukocytes, CD203c appears to be selectively expressed on the basophil/mastocytes lineage. Prior to the present invention, CD203c had been used to evaluate IgE mediated hypersensitivity to latex and aeroallergens (Boumiza, 2002; Hauswirth, 2002). For example, Boumiza et al. compared basophil activation tests using either CD63 or CD203c in the diagnosis of latex allergy and found that the sensitivity was considerably higher with CD203c (75% compared to 50% with CD63) (Boumiza, 2002), likely due to superior recognition of basophils using CD203c, and the higher level of expression of CD203c in activated basophils as compared to CD63. Without being bound by theory, the present inventors propose that the difference in response between CD203c and CD63 can also be explained by their different mechanism of upregulation. For example, PGD2 is a strong inducer of CD203c expression. However, it does not stimulate CD63 expression (15). The kinetics of upregulation of CD203c is fast and peaks after 5-15 minutes, whereas that of CD63 is slow and peaks after 20-40 min (Hennersdorf, 2005). CD203c is expressed on both resting and activated basophils and is upregulated in response to cross-linking of the FcεRIα receptor (Binder, 2002).

Some recently identified surface markers follow the upregulation kinetics of either CD203c or CD63 (CD13, CD164 and CD107a). The upregulation of CD13 and CD164 is fast and similar to that of CD203c and accordingly, these two proteins represent additional markers that can be used as an alternative to or in addition to the use of CD203c to identify patients with autoimmune chronic urticaria as described herein. On the other hand, the surface increase of CD107a is slow and follows the kinetics of CD63 (Monneret, 2005).

Accordingly, one embodiment of the present invention relates to a method to diagnose autoimmune chronic urticaria in a patient. The method includes a first step of contacting isolated cells that express CD203c and FcεRI (e.g., mast cells or basophils, and most preferably, basophils) with a test biological sample from a patient being diagnosed for autoimmune chronic urticaria. The isolated cells upregulate CD203c expression after stimulation either via the FcεRI and/or by a different type of stimulation that is sufficient to upregulate CD203c (e.g., with a granulocyte activating reagent, such as fMLP). The method further includes a second step of detecting expression of CD203c expression on the cells. Upregulation of CD203c on the cells in the presence of the test biological sample, as compared to CD203c expression on the cells in the absence of contact with the biological sample, and/or as compared to CD203c expression on the cells when contacted with a normal control sample, indicates that the patient has autoimmune chronic urticaria. In other embodiments of this invention, CD13 or CD164 may be substituted for CD203c. In another embodiment, the method can include detection of any one or more of CD13, CD164 and CD63, in addition to the detection of CD203c, which may be performed simultaneously with the detection of CD203c or sequentially. In additional embodiments, the method can include detection of functional auto-antibodies by histamine release using a basophil histamine release (BHR) assay and/or an autologous serum skin test (ASST).

Chronic urticaria (CU) is a disease defined by a period of whealing (welts, hives) lasting for weeks to many years. Urticaria is a vascular reaction, usually transient, involving the upper dermis, representing localized edema caused by dilatation and increased permeability of the capillaries, and marked by the development of wheals. The lesions are usually pruritic. The causes of chronic urticaria can include, infectious disease, malignancy, allergic reactions, pseudoallergic reactions, and autoimmunity. Autoimmune chronic urticaria is the subject of the present invention, and refers to chronic urticaria that is associated with the presence in the individual of autoantibodies, particularly autoantibodies against the high affinity IgE receptor (FcεRI), although anti-IgE antibodies may also contribute to the disease. These autoantibodies are believed to cross-link the α subunits of FcεRI on mast cells or basophils, resulting in the degranulation of the cells and release of histamine. Although anti-FcεRI are found in patients with a variety of autoimmune disorders, in autoimmune chronic urticaria, the antibodies are identified as "functional" for causing the degranulation of basophils and mast cells, as well as histamine release. Functional anti-FcεRI antibodies are typically identified by autologous serum skin testing (ASST) and may be confirmed by histamine release (HR) assays, immunoblotting, or ELISA. The present invention provides a rapid and sensitive assay that has been demonstrated to correlate in specificity and sensitivity with these known tests for functional anti-FcεRI antibodies, but is less invasive and time consuming than these assays.

The first step in the method of the present invention includes a step of contacting isolated cells that express the marker of interest (i.e., CD203c and/or in some embodiments, CD13, CD164 and/or CD63) and FcεRIα with a test biological sample from a patient being diagnosed for autoimmune chronic urticaria. In general, any methods or techniques described herein for CD203c can be applied to other markers to be used in the alternative, or in addition to, the CD203c marker of the invention. The cells to be used in the assay of the present invention can be any cells that express the marker of interest (i.e., CD203c and in some embodiments, CD13, CD164 and/or CD63) and FcεRIα, or that express functional portions of the marker of interest and/or the FcεRIα, and that upregulate the expression of the marker (e.g., CD203c) upon stimulation of FcεRIα, such as by cross-linking of FcεRIα. Such cells can be identified by exposing a candidate cell to anti-FcεRI (and particularly anti-FcεRIα) and/or to another reagent that stimulates the activation of the cell (e.g., a granulocyte stimulator, such as fMLP), whereby such exposure results in upregulation of expression of the marker (e.g., CD203c).

In one aspect of the invention, the cells used in the assay are mast cells or basophils, with basophils being particularly preferred. One advantage of the present invention is that the cells, and particularly basophils, can be provided in the form of whole blood or a fraction thereof from a selected donor (described below), because the assay, being based on the detection of a marker that is selective for basophils and mast cells (e.g., CD203c), will specifically detect basophil and basophil degranulation (e.g., specifically related to autoimmune chronic urticaria) without the need to separate the basophils from other peripheral blood cells. However, the present invention also contemplates the provision of suitable cells in any form, including in whole blood, in a fraction thereof (e.g., peripheral blood cells isolated therefrom), as a partially or substantially purified sample of basophils (or mast cells or other suitable cells), or as a cell line (e.g., isolated, cloned, immortalized, genetically modified, etc.).

In one aspect of the invention, the cells can be isolated from a single donor or from multiple donors, as long as the cells upregulate expression of CD203c (or another desired marker) upon stimulation of FcεRIα. Preferably, the cells have been selected to upregulate expression of CD203c upon stimulation: of FcεRIα and, if the cell is a basophil, upon stimulation of FcεRIα and/or a granulocyte stimulator, such as FMLP. Particularly preferred cells to use in an assay of the invention are cells meeting the above criteria that are upregulate CD203c to a significant degree upon stimulation of FcεRI so that the result of testing in the assay can be clearly distinguished above background CD203c expression. In particular, cells can be selected from among a pool of possible cells (e.g., cells from different donors can be screened) that upregulate CD203c in response to stimulation of FcεRI (and perhaps also using another stimulator, such as FMLP) to a statistically more significant degree than the other cell samples in the pool. The skilled practitioner will readily be able to select a suitable donor. Preferably, the donor from which the cells used in the assay are obtained or derived does not have autoimmune chronic urticaria, and more preferably, does not have any form of urticaria. In one embodiment, the donor is non-atopic, although atopic donors may also be used.

An example of a method to select a suitable donor cell is described in the Examples section. For example, whole blood from a panel of potential donors can be screened for sufficient upregulation of CD203c on basophils (CD203c/IgE positive cells) in response to a known stimulator of CD203c (e.g., fMLP) and a known stimulator of FcεRIα (e.g., anti-FcεRIα antibody or another agent that engages or cross-links the receptor). Preferably, the expression of CD203c is upregulated on the cell in response to a known stimulator of CD203c at least 5%, and more preferably, at least 30%, and even more preferably, at least 50% (or any percentage in between, in whole number increments—at least 5%, at least 6%, etc.), as compared to the expression of CD203c in the absence of the known stimulus of CD203c (e.g., fMLP) or as compared to the normal (negative or background) control. Alternatively, the expression of CD203c is upregulated on the cell in response to a known stimulator of CD203c at least 1.5 fold, and more preferably, at least 3 fold, and even more preferably, at least 6 fold, as compared to the expression of CD203c in the absence of the known stimulus of CD203c (e.g., fMLP) or as compared to the normal (negative or background) control. These criteria for CD203c expression can also be used to identify other cells that are useful in the present invention (e.g., cell lines). These criteria can also be used with other markers described herein (e.g., CD13, CD164 and/or CD63) to identify cells useful for screening for these markers, although identifying a cell based on CD203c expression is believed to be sufficient to screen for these other markers, if desired.

The cells selected for use in the present invention can be obtained repeatedly from a given donor source(s), immortalized or otherwise prepared as cell lines that can be repeatably cultured, maintained, frozen, rethawed, and/or stored, and then used in the method of the invention. One may also use a publicly available cell line that meets the criteria of upregulating CD203c upon stimulation as described herein. For example, a basophil cell lines derived from a patient with myelogenous leukemia are available through the American Type Culture Collection (ATCC®) as ATCC Deposit Nos. CRL-2099™, CRL-2100™ and CRL-2101™.

As discussed above, CD203c belongs to the type II transmembrane protein family and is a multifunctional ecto-enzyme called ectonucleotide pyrophosphatase phophodiesterase 3 (E-NPP3) that catalyzes the cleavage of a number of molecules including deoxynucleotides and nucleotide sugars. It also contains a somatomedin B-like domain and a cell adhesive motif, and among leukocytes, is selectively expressed on the basophil/mastocytes lineage. The nucleic acid and amino acid sequences for human CD203c are known in the art (e.g., see Accession No. gi:4826896 (amino acid sequence) and Accession No. gi:25453478 (nucleic acid sequence), both of which are incorporated herein by reference in their entireties).

CD13 (also known as human aminopeptidase-N) is a zinc-binding aminopeptidase-N enzyme expressed on the surface of early committed progenitors of granulocytes and monocytes (CFU-GM) and by all cells of these lineages as they mature (including on activated basophils), on endothelial cells, epithelial cells from renal proximal tubules and intestinal brush border, bone marrow stromal cells, osteoclasts, and cells lining bile duct canaliculi, and on a small proportion of large granular lymphocytes (Soderberg et al 1993) but not other lymphocytes. The nucleic acid and amino acid sequences for human CD13 are known in the art (e.g., see Accession No. gi:4502095 (amino acid sequence) and Accession No. gi:4502094 (nucleic acid sequence), both of which are incorporated herein by reference in their entireties).

CD164 (also known as sialomucin) is a mucin-like receptor, or sialomucin, expressed by human CD34+ hematopoietic progenitor cells and is expressed by activated basophils. Its functions include mediating, or regulating, haematopoietic progenitor cell adhesion and the negative regulation of their growth and/or-differentiation. The nucleic acid and amino acid sequences for human CD164 are known in the art (e.g., see Accession No. gi:21361274 (amino acid sequence) and Accession No. gi:34222157 (nucleic acid sequence), both of which are incorporated herein by reference in their entireties).

CD63 is a member of the transmembrane-4 superfamily, and is expressed on many cells in the peripheral blood, including on activated basophils and mast cells as a result of the fusion between intracytoplasmic granules and the plasma membrane. The nucleic acid and amino acid sequences for human CD63 are known in the art (e.g., see Accession No. gi:4502679 (amino acid sequence) and Accession No. gi:34328936 (nucleic acid sequence), both of which are incorporated herein by reference in their entireties).

Human FcεRIα is the high affinity receptor for immunoglobulins of the IgE isotype. The amino acid and nucleic acid sequences encoding the components of this receptor are known in the art, and the three-dimensional structure of FcεRIα has been solved (e.g., see Garman et al., 1998, *Cell* 95(7):951-961 (structure denoted IF2Q); Garman et al., 2000, *Nature* 406(6793):259-266 (structure denoted IF6A); and Garman et al., 2001, *J. Mol. Biol.,* 311(5):1049-62).

The conditions under which a cell that expresses CD203c (or another marker described herein) is contacted with a patient test sample, such as by mixing, are conditions in which the expression of CD203c is not stimulated (activated) or upregulated if essentially no test sample is present. For example, such conditions include normal culture conditions in the absence of a known activating compound or other equivalent stimulus of expression of CD203c, and in the case of basophils, of basophil degranulation. The patient test sample is then contacted with the cells. Effective culture conditions include, but are not limited to, appropriate media, temperature, pH and oxygen conditions that permit the growth of the cells used in the test. An appropriate, or effective, medium is typically a medium comprising growth factors and assimilable carbon, nitrogen and phosphate sources, as well as appropriate salts, minerals, metals and other nutrients, such as vitamins. Culturing is carried out at a temperature, pH and oxygen content appropriate for the cell. Such culturing conditions are within the expertise of one of ordinary skill in the art.

A patient sample most typically includes any bodily fluid (although cell or tissue samples are not excluded) that may contain functional autoantibodies against FcεRIα (i.e., an anti-FcεRI that upregulates CD203c and causes degranulation of granulocytes, and particularly, basophils). More specifically, according to the present invention, the term "test sample" or "patient sample" or "test biological sample" can be used generally to refer to a sample of any type which contains, or may contain, the antibodies to be evaluated by the present method, including but not limited to, a sample of isolated cells, a tissue sample and/or a bodily fluid sample. According to the present invention, a sample of isolated cells is a specimen of cells, typically in suspension or separated from connective tissue which may have connected the cells within a tissue in vivo, which have been collected from an organ, tissue or fluid by any suitable method which results in the collection of a suitable number of cells for evaluation by the method of the present invention. A tissue sample, although similar to a sample of isolated cells, is defined herein as a section of an organ or tissue of the body which typically includes several cell types and/or cytoskeletal structure which holds the cells together. One of skill in the art will appreciate that the term "tissue sample" may be used, in some instances, interchangeably with a "cell sample", although it is preferably used to designate a more complex structure than a cell sample. A tissue sample can be obtained by a biopsy, for example, including by cutting, slicing, or a punch. A bodily fluid sample, like the tissue sample, contains the cells to be evaluated for marker expression or biological activity and/or may contain a soluble biomarker that is secreted by cells, and is a fluid obtained by any method suitable for the particular bodily fluid to be sampled. Bodily fluids suitable for sampling include, but are not limited to, blood, mucous, seminal fluid, saliva, breast milk, bile and urine. The present invention will most typically use a whole blood or serum sample from a patient, and most preferably uses a serum sample.

The period of contact of the cells with the patient sample being tested can be varied, and can be determined by one of skill in the art. For example, the period of contact can be minutes or hours, and is typically performed in from about 5 to 60 minutes. As used herein, the term "contact period" refers to the time period during which cells are in contact with the patient sample being tested. The term "incubation period" refers to the entire time during which cells are allowed to grow or bind to an agent prior to evaluation, and can be inclusive of the contact period. Thus, the incubation period includes all of the contact period and may include a further time period during which the patient sample being tested is not present but during which expression of CD203c is allowed to continue or is stopped prior to scoring.

According to the present invention, the method includes the step of detecting the expression of CD203c (or another marker) in the cells. This step can include determining whether CD203c expression is upregulated as compared to a control, downregulated as compared to a control, or unchanged as compared to a control. Therefore, the step of detecting expression does not require that expression of CD203c actually is upregulated, but rather, can also include detecting that the expression of CD203c has not changed (i.e., detecting no upregulation of expression of CD203c or detecting non-significant upregulation of expression of CD203c).

Methods to measure CD203c expression or to detect expression levels of any protein marker generally include, but are not limited to: flow cytometry, fluorescence activated cell sorting (FACS), enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, and/or microcytometry, microscopy. In one aspect of the invention, CD203c expression is detected using flow cytometry. In one aspect, two or more markers are simultaneously detected (e.g., CD203c and CD63; CD203c and CD13 and/or CD164, etc.).

In one embodiment, the CD203c (or other marker) is detected using an antibody or antigen-binding fragment thereof that selectively binds to the CD203c (or other marker). Antibodies that selectively bind to CD203c can be produced using CD203c protein information available in the art. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.). In one embodiment, antibodies that bind to an epitope (linear or conformational) of the long form, but not the short form, of FBLN-3 are envisioned. Such antibodies typically bind to an epitope that comprises at least a portion of the extracellular domain of CD203c.

Antibodies useful in the test kit and methods of the present invention can include polyclonal and monoclonal antibodies, divalent and monovalent antibodies, bi- or multi-specific antibodies, serum containing such antibodies, antibodies that have been purified to varying degrees, and any functional equivalents of whole antibodies. Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

The invention also extends to non-antibody polypeptides, sometimes referred to as antigen binding partners or antigen binding peptides, that have been designed to bind selectively to the protein of interest (e.g., CD203c). Examples of the design of such polypeptides, which possess a prescribed ligand specificity are given in Beste et al. (*Proc. Natl. Acad. Sci.* 96:1898-1903, 1999), incorporated herein by reference in its entirety.

Methods of detecting CD203c (or another marker) expression may also include detecting transcription of the marker in the donor cells. Such a method can include, but is not limited to, extraction of cellular mRNA and Northern blotting using labeled probes that hybridize to transcripts encoding all or part of a gene encoding the marker (e.g., CD203c); amplification of mRNA using marker-specific primers, polymerase chain reaction (PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of a gene encoding CD203c; in situ hybridization; and detection of a reporter gene. Other methods of detecting transcription are known in the art and can be applied here.

According to the present invention, a probe or primer is a nucleic acid molecule which typically ranges in size from about 8 nucleotides to several hundred nucleotides in length. Such a molecule is typically used to identify a target nucleic acid sequence in a sample by hybridizing to such target nucleic acid sequence under stringent hybridization conditions. As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

Agents useful for detecting expression of a marker of the present invention can be conjugated to a detectable tag or detectable label. Such a tag can be any suitable tag which allows for detection of the marker using the selected technique (described above) and includes, but is not limited to, any composition or label detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

According to the present invention, a "control level" of CD203c expression (or another marker) is a baseline level, and in some embodiments (but not all embodiments, depending on the method), a normal or negative level, of CD203c expression against which a test level of expression (i.e., in the test sample) can be compared. Therefore, it can be determined, based on the control or baseline level of CD203c expression, whether a sample to be evaluated causes a measurable increase or substantially no change in CD203c expression in the cells included in the test, as compared to the negative baseline level. In one aspect, the baseline level is a negative or normal control level that is indicative of the CD203c expression expected from contact with a normal (i.e., healthy, negative control, non-autoimmune chronic urticaria) biological sample. Therefore, the term "negative control" used in reference to a baseline level of CD203c expression typically refers to a baseline level established from a sample from a population of individuals which is believed to be normal (i.e., healthy, not suffering from autoimmune CU). It is noted that exposure of the cells to the "negative control" results in a lower level of CD203c expression than would be detected from exposure to a sample from a patient with autoimmune CU.

In another embodiment, a "positive control" baseline is used (including in addition to the negative control), which refers to a level of CD203c expression established by exposing the cells in the assay to a known stimulator of FcεRI cross-linking and/or a known stimulator of CD203c expression (e.g., anti-FcεRI and fMLP), or to a sample from a patient that is known to have autoimmune CU. It is noted that this "positive control" will most typically induce have a higher level of CD203c expression than in a normal or negative control sample.

It will be appreciated by those of skill in the art that a baseline need not be established for each assay as the assay is performed but rather, a baseline can be established by referring to a form of stored information regarding a previously determined baseline level of CD203c expression for a given control sample with the same test cells. Such a form of stored information can include, for example, but is not limited to, a reference chart, listing or electronic file of population or individual data regarding "normal" (negative control) or positive CD203c expression, or any other source of data regarding baseline CD203c expression that is useful for the patient to be diagnosed.

A positive diagnosis indicates that the patient has, is developing, or is at risk of developing, autoimmune chronic urticaria. In order to establish a positive diagnosis, the level of CD203c expression is increased over the established baseline by an amount that is statistically significant (i.e., with at least a 95% confidence level, or p<0.05). The values obtained from the test and/or any control samples are statistically processed using any suitable method of statistical analysis to establish a suitable baseline level using methods standard in the art for establishing such values. Preferably, detection of at least about a 5-10% change in CD203c expression in the sample as compared to the baseline level results in a positive diagnosis. More preferably, detection of at least about a 30% change in CD203c expression from the sample as compared to the baseline level results in a positive diagnosis. More preferably, detection of at least about a 50% change, and more preferably at least about a 70% change, and more preferably at least about a 90% change, or any percentage change between 5% and higher in 1% increments (i.e., 5%, 6%, 7%, 8% . . . ) in CD203c expression induced by the sample as compared to the baseline level results in a positive diagnosis of autoimmune chronic urticaria for the test sample, and therefore, for the patient. In one embodiment, a 1.5 fold change in CD203c expression induced by the sample as compared to the baseline level results in a positive diagnosis. More preferably, detection of at least about a 3 fold change, and more preferably at least about a 6 fold change, and even more preferably, at least about a 12 fold change, and even more preferably, at least about a 24 fold change, or higher, or any fold change from 1.5 and higher in increments of 0.5 fold (i.e., 1.5, 2.0, 2.5, 3.0 . . . ) in CD203c expression as compared to the baseline level, results in a positive diagnosis of autoimmune chronic urticaria. These criteria can also be used to evaluate other markers described herein (e.g., CD13, CD164, CD63).

In one embodiment of the method of the present invention, as discussed above, in addition to evaluating the expression of CD203c in response to contact with an individual's test biological sample, one can additionally or alternatively evaluate a change in expression of CD13 and/or CD164 in the test cells in response to contact with the individual's test biological sample. Detection of an increase in expression of either CD13 or CD164 in cells after contact with the test biological sample, as compared to CD13 or CD164 expression, respectively, on the cells in the absence of contact with the biological sample, or as compared to CD13 or CD164 expression, respectively, on the cells when contacted with a negative control sample from an individual who does not have autoimmune chronic urticaria, indicates that the patient has autoimmune chronic urticaria. If used together with CD203c detection, these markers can be detected at the same time as CD203c (e.g., by multiple labeling using flow cytometry) or in sequential steps.

In another embodiment of the method of the present invention, in addition to evaluating the expression of CD203c (and/or CD13 and/or CDD164) in response to contact with an individual's test biological sample, one can evaluate any one or more of: CD63 expression by the test cell in response to contact with the biological sample; histamine release in response to contact with the biological sample, or autologous serum skin test reactions using the biological sample. Methods of CD63 detection are as described herein for CD203c, or can be performed as described previously (Wedi, 2000; Gyimesi, 2004). The histamine release assay (HR or BHR) is performed as described in the Examples or as previously described (Ferrer, 1999; Platz er et al., 2005, "Validation of basophil histamine release against the autologous serum skin test and outcome of serum-induced basophil histamine release studies in a large population of chronic urticaria patients", Allergy 60:1152-6). An autologous serum skin test (ASST) is performed as described in the Examples or as previously described (Platzer et al., supra; Sabroe, 1999). Such additional evaluations are used to confirm, or further validate, the results of the method of the present invention, but are not required to practice the method of the present invention.

Another embodiment of the invention relates to test or assay kits containing the reagents necessary to evaluate a patient for autoimmune chronic urticaria using the method of the invention. Such reagents will be apparent to those of skill in the art given the present disclosure. For example, such a test kit may include, (a) cells (e.g., basophils) for use in the assay (e.g., that upregulate CD203c expression after stimulation with a granulocyte activating reagent and/or after stimulation of FcεRIα on the cells); and (b) a reagent for the detection of CD203c expression on the cells (e.g., either by detection of protein expression or detection of transcription of RNA encoding CD203c). For example, the reagent for detection of CD203c expression on the cells can include, but is not limited to, a CD203c antibody or antigen-binding fragment thereof, such as a monoclonal antibody, or probes or primers useful for the detection of CD203RNA. The kit may further include other useful reagents, such as a means for detecting the binding of the antibody to CD203c (e.g., a secondary antibody, a label, an enzyme, etc.). The kit may further include positive control reagents (e.g., fMLP and anti-FcεRIα) and/or a negative control reagent (e.g., a buffer). The kit may include reagents for detecting other markers described herein (e.g., CD13, CD164, CD63), or reagents useful for performing a BHR (e.g., reagents for the detection of histamine) or ASST.

The kit preferably contains any means of detecting the expression or activity of a CD203c, and preferably includes a probe; PCR primers; or an antibody, antigen binding peptide, or fragment thereof, that binds to CD203c or a gene encoding CD203c. The kit can include any reagent needed to perform a diagnostic method envisioned herein. The antibody, or fragment thereof, can be conjugated to another unit, for example a marker or immobilized to a solid carrier (substrate). The kit can also contain a second antibody for the detection of CD203c:antibody complexes. In one embodiment, the kit can contain a reagent for detecting a control marker characteristic of a given cell type (e.g., an antibody or antigen binding fragment thereof). The antibody or fragment thereof, or a probe or primer, may be present in free form or immobilized to a substrate such as a plastic dish, a test tube, a test rod and so on. The kit can also include suitable reagents for the detection of and/or for the labeling of positive or negative controls, wash solutions, dilution buffers and the like, as well as instructions for using the assay kit.

Another embodiment of the invention relates to the use of CD203c as a target for the development of therapeutic compositions and to strategies and methods for the prevention and/or treatment of autoimmune chronic urticaria. Such a method includes, for example, administering to the patient a pharmaceutical composition that inhibits the binding of autoantibodies to FcεRIα and/or inhibits the activation of the basophil or mast cell, and particularly the degranulation of such cells, which can be monitored by evaluating the expression of CD203c. Such compounds, by inhibiting expression of CD203c directly or indirectly can be useful for treating or preventing autoimmune chronic urticaria. Such compounds can include, but are not limited to, antibodies and antigen-binding fragments thereof, small molecules, proteins and peptides, RNAi, aptamers, ribozymes and antisense nucleic acid molecules.

RNA interference (RNAi) is a process whereby double stranded RNA, and in mammalian systems, short interfering RNA (siRNA) or short hairpin RNA (shRNA), is used to inhibit or silence expression of complementary genes. In the target cell, siRNA are unwound and associate with an RNA induced silencing complex (RISC), which is then guided to the mRNA sequences that are complementary to the siRNA, whereby the RISC cleaves the mRNA. shRNA is transfected into a target cell in a vector where it is transcribed, and then processed by DICER enzymes to form siRNA-like molecules that activate RISC, which, as with siRNA, is then guided to the mRNA sequences that are complementary to the shRNA, whereby the RISC cleaves the mRNA.

Aptamers are short strands of synthetic nucleic acids (usually RNA but also DNA) selected from randomized combinatorial nucleic acid libraries by virtue of their ability to bind to a predetermined specific target molecule with high affinity and specificity. Aptamers assume a defined three-dimensional structure and are capable of discriminating between compounds with very small differences in structure.

A ribozyme is an RNA segment that is able to perform biological catalysis (e.g., by breaking or forming covalent bonds). More specifically, ribozymes are antisense RNA molecules that function by binding to the target RNA moiety and inactivate it by cleaving the phosphodiester backbone at a specific cutting site.

Pharmaceutical compositions for use in accordance with the present invention can be formulated in conventional manner using one or more physiologically acceptable carriers comprising excipients and auxiliaries which facilitate processing of the active compounds into preparations which can be used pharmaceutically. Proper formulation is dependent upon the route of administration chosen.

One may use CD203c (or CD13 or CD164) as a target marker for the identification of therapeutic compounds that inhibit or prevent degranulation and histamine release by cells that are typically targeted by the autoantibodies of autoimmune CU patients (e.g., basophils). As used herein, the term "putative" or "candidate", when used with regard to a regulatory compound, refers to compounds having an unknown regulatory activity, at least with respect to the ability of such compounds to regulate expression of a gene or protein or the biological activity of a protein as described herein. In the method of identifying a regulatory compound according to the present invention, the method can be a cell-based assay, or non-cell-based assay.

For example, this method can be performed in a cell-based assay using substantially the same method as the diagnostic assay, except that the cells are stimulated by a known stimulator of CD203c (e.g., fMLP and anti-FcεRI, or a sample from a patient known to have autoimmune chronic urticaria), instead of with a test biological sample. The cells are also contacted with a putative regulatory compound, either before stimulation of the cells (to determine the ability of the compound to prevent upregulation of expression of the CD203c) or simultaneously with or after stimulation of the cells (to determine the ability of the compound to reduce/inhibit/downregulate upregulation of expression of CD203c). The assay then includes a step of detecting whether the putative regulatory compound prevents or reduces (or downregulates) the upregulation of CD203c on the cells in response to the known stimulus. In this method, CD203c serves as a marker to indicate that the characteristics of activation of the test cell are inhibited or prevented by the putative regulatory compound. Since the present inventors have shown that upregulation of CD203c on a basophil correlates with histamine release, this assay is believed to be a reasonable indicator of compounds that can inhibit basophil activation and/or histamine release by the basophil (or mast cell). Compounds that prevent or reduce the upregulation of expression of CD203c by a cell are identified as compounds that are candidates for inhibiting (ameliorating, reducing the symptoms or recurrence of) autoimmune chronic urticaria in a patient. Such compounds can then be further validated using other assays (e.g., using other markers or tests described herein) and in clinical trials.

One may also identify compounds that bind to CD203c (e.g., such as by an immunoassay or other binding assay), or bind to a nucleic acid molecule encoding 203c (e.g., RNAi, ribozymes, antisense, or inhibitors of transcription or translation of CD203c RNA or protein), or regulate the activity of CD203c (e.g., regulates the enzymatic activity of the protein) using a non-cell based assay. Such assays will be apparent to those of skill in the art given the target marker.

Compounds identified using such methods of the invention can be used to reduce or prevent the symptoms of autoimmune chronic urticaria in an individual. Such compounds can include proteins, polypeptides, nucleic acid molecules, antibodies and binding fragments thereof, and small molecules (e.g., products of drug design or screening).

According to the present invention, the methods of the present invention are suitable for use in an individual or with the cells or biological sample of an individual that is a member of the Vertebrate class, Mammalia, including, without limitation, primates, livestock and domestic pets (e.g., a companion animal). Most typically, an individual will be a human individual. The term "individual" can be interchanged with the term "subject" or "patient" and refers to the subject of a protocol or method according to the invention. Accordingly, an individual can include a healthy, normal (non-diseased) individual, as well as an individual who has or is at risk of developing autoimmune chronic urticaria or a symptom or indicator thereof as described herein.

Various aspects of the invention are described in the following example; however, the following example is provided for the purpose of illustration and are not intended to limit the scope of the present invention.

EXAMPLES

The following Materials and Methods were used in Examples 1-4 below.

Patients and Controls

Chronic urticaria (CU) was defined as recurrent wheals occurring at least 3 times per week for more than 6 weeks without an identifiable cause. Patients were excluded if they had evidence of a known trigger or, cause, including physical urticaria, urticarial vasculitis or allergic cause of their hives. Sera were obtained from thirty-two patients with CU at the time of ASST and stored at −80° C. Antihistamines were held for at least 48 hours prior to collection of sera. Eleven sera from healthy adult individuals were used as normal controls. Four sera with a high titer ANA ≧1:360, 3 with a history of active connective tissue disease, and the other with eosinophilic gastroenteritis, were used for disease controls. The study was approved by the Institutional Review Board at the National Jewish Medical and Research Center.

ASST

The test was performed by injecting 0.05 cc of the patient's own serum intradermally into the volar aspect of the forearm.

Sterile saline and histamine were used as negative and positive controls, respectively. Wheal and flare reactions were measured at 30 minutes. A mean wheal diameter ≧2 mm than the control was considered to be a positive ASST.

Basophil Donor

Whole blood from seven normal individuals was screened and one donor was identified based on the marked upregulation of CD203c on basophils (CD203c/IgE positive cells) in response to FMLP and anti-FcεRIα antibody. The basophil donor was atopic and had a serum IgE level of 154 kU/L. The basophil donor provided informed consent and was bled ≦1 time per week.

IgG Depletion

Selected patients and normal control patients sera were depleted of IgG using a protein G-Sepharose column (Sigma, St. Louis, Mo.). Pre and post IgG depletion levels were measured by nephelometry (Immage Immunochemistry System, Beckman Coulter, Fullerton, Calif.). All sera had post depletion levels of <33.3 mg/dL (the lowest level of detection by nephelometry). Dilution of sera passing through the column was accounted for by measuring serum albumin levels pre and post depletion.

Antibodies

The following monoclonal antibodies were used: phycoerythrin (PE)-conjugated anti-human CD203c (Beckman Coulter, Fullerton, Calif.), peridinin chlorophyll protein complex (PerCP)-conjugated anti-human CD45 (BD Bioscience, San Jose, Calif.), and flourescein isothiocyanate (FITC)-conjugated anti-human IgE (Caltag, Burlingame, Calif.).

Measurement of CD203c Surface Expression

The test was carried out on heparinized blood within 3-4 hours after drawing the donor's blood. Two hundred µL aliquots of the donor's heparinized whole blood were incubated for 10 minutes at 37° C. with 40 µL of sera from CU patients, normal controls, or IgG depleted sera. For controls, 40 µL basophil stimulation buffer (20 mM HEPES, 125 mM NaCl, 5 mM KCl, 2.5 mM $CaCl_2$, 1 mM $MgCl_2$, 0.5 mM glucose, and 0.1% BSA, pH 7.4) was added to 200 µL of donor's blood and used as the negative control while 40 µL of -2 µM f-Met-Leu-Phe (fMLP, Sigma, St. Louis, Mo.) and 40 µL of a 1:50 dilution of anti-FcεRIα receptor antibody (Upstate, Charlottesville, Va.) in Ca++ and Mg++ free phosphate buffered saline (PBS) was used as positive controls. The reactions were stopped by placing the tubes on ice. Cells were then stained with PE-anti-human CD203c, PerCP-anti-human CD45, and FITC-anti-human IgE at 4° C. in the dark for 30 minutes. Red cells were lysed with FACS Lysing Solution (Becton Dickinson, San Jose, Calif.). The cells were then washed once with 2 ml of PBS and fixed in 1% formaldehyde. The cells were then analyzed on a FACSCalibur flow cytometer (Becton Dickinson, San Jose, Calif.).

Flow Cytometry

Basophils from whole blood were identified by the presence of CD203c on high expressing IgE positive cells (FIGS. 1A and 1B). The data are expressed as the mean fluorescence intensity or the percentage of CD203c expression. Percent CD203c expression is defined as the percent of basophils expressing more CD203c than ≧99% of basophils incubated with buffer only. This was determined by defining an M1 region on the histogram analysis (FIG. 1C).

Basophil Histamine Release (BHR)

Whole blood from the same donor for the CD203c assay was collected in a heparinized tube and BHR carried out according to the manufacturer's instructions (Beckman Coulter, Fullerton, Calif.). For the BHR whole blood was diluted 1:7 in the histamine release buffer. Fifty µL of stimuli including patients sera, anti-FcεRI (as a positive control), or histamine release buffer (as a negative control) was added to 100 µL of blood and incubated at 37° C. for 30 minutes. To determine total histamine, whole blood was diluted 1:20 in distilled water followed by two rapid freeze thaw cycles. Histamine concentrations in the supernatants of centrifuged blood were performed by ELISA (Beckman Coulter, Fullerton, Calif.) according to the manufacturer's instructions. Spontaneous histamine release was determined by the amount of histamine released by cells incubated with the histamine release buffer. Spontaneous release was <5% of total release. Positive histamine release was defined as >15% of total release (Ferrer, 1999).

Antinuclear Antibody Determination

Anti-nuclear antibodies (ANAs) were detected by indirect immunofluorescence with HEp-2 cells (Bio-Rad Laboratories, Redmond, Wash.).

Statistics

Significant differences between groups were analyzed using a two-tailed unpaired t-test. Correlation was determined using Pearson Product Moment correlation. Sensitivity, specificity, negative and positive predictive value were also calculated.

Example 1

The following example demonstrates that CD203c expression on basophils from chronic urticaria patients is elevated.

Figure 2:
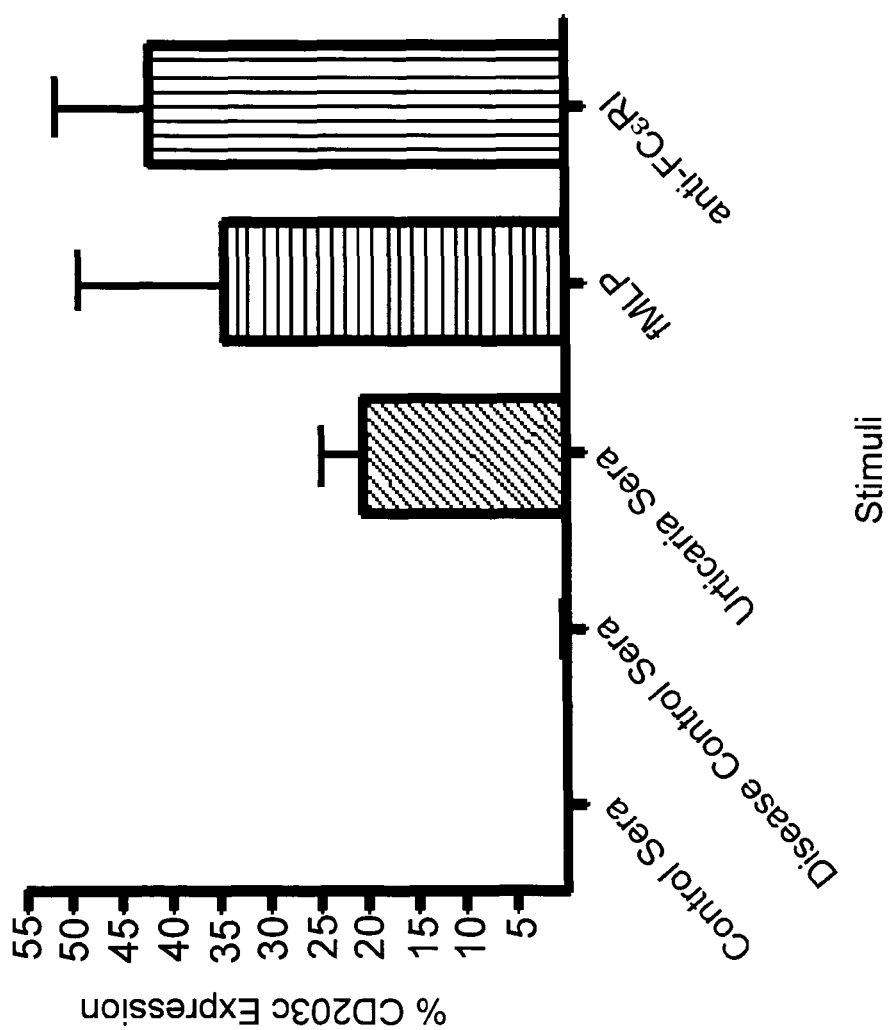
FIG. 2 shows the mean percent (±SEM) CD203c expression above baseline by sera from normal controls (N=11), disease controls (N=4), all CU patients (N=32), and positive controls (i.e., fMLP and anti-FcεRI).

CD203c expression was higher in basophils incubated with sera from CU patients compared to normal control individuals (FIG. 2). The mean percent basophil CD203c expression of 11 normal control individuals was −0.6%±0.1 (±SEM) versus 20%±4 in 32 CU patients (p=0.002). Sera from patients with high-titer ANAs (disease controls) did not induce basophil CD203c expression. The mean values of the positive controls fMLP and anti-FcεRIα were 34.5%±14.6 and 41.9%±9.4 (n=4), respectively.

Figure 3:
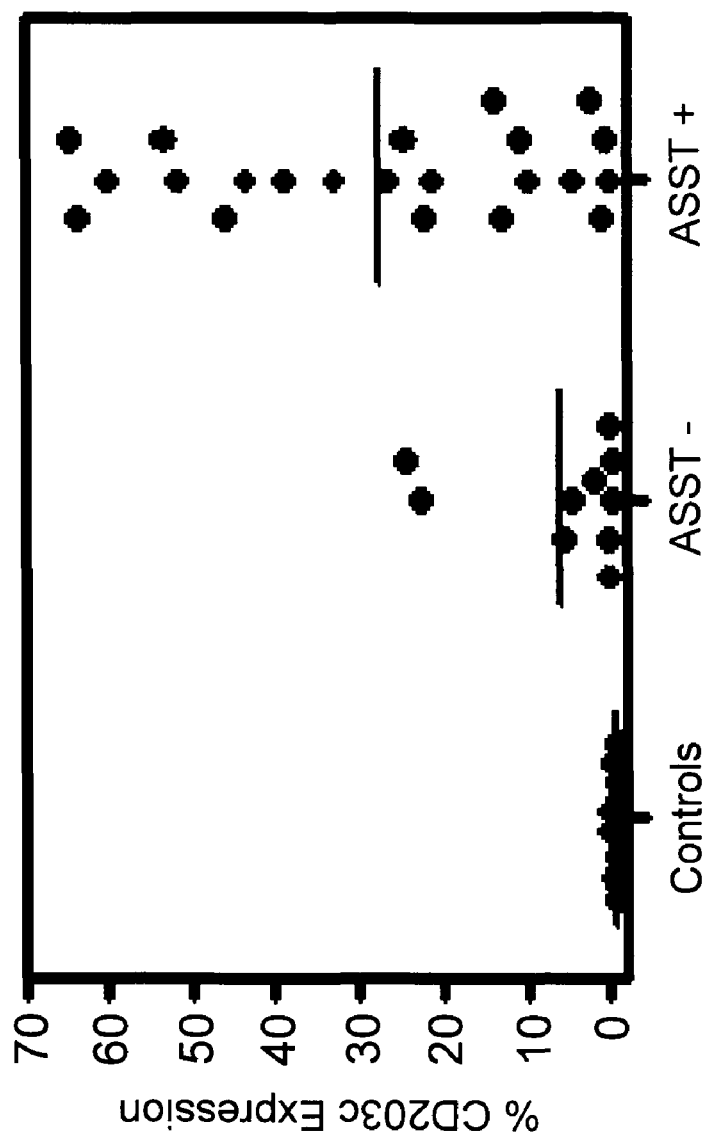
FIG. 3 shows the percent CD203c expression by normal individuals, CU patients with negative ASST, and CU patients with positive ASST (horizontal bars represent means).

CD203c expression was significantly higher after incubation of basophils with sera from ASST positive CU patients than normal control sera (p<0.001) (FIG. 3). The mean percent CD203c expression was 30%±5 (SEM) (n=22) in basophils incubated with positive ASST positive CU sera versus −0.6%±0.1 for normal control sera (n=11). The range of percent CD203c expression in cells incubated with ASST positive serum was −0.1% to 63.3%. Seventeen of twenty-two ASST positive sera (77%) resulted in basophil activation of greater than 5%. The range of percent basophil activation in cells incubated with normal control serum was −1.2% to 0.0% compared to buffer control. CD203c expression was also significantly higher in basophils incubated with ASST positive sera than with ASST negative sera (p=0.006). The mean percent CD203c expression was 30%±5 versus 6%±3 respectively. The range of CD203c expression for basophils incubated with ASST negative sera was 0.1% to 24%. Eight of 10 ASST negative sera resulted in CD203c expression of ≦5%, and the other two resulted in 22% and 24% expression. Incubation with ASST negative sera also resulted in significantly higher CD203c expression than control sera (p=0.04). Two patients with negative autologous serum skin tests (ASST) and sera that induced an elevation of CD203c of over 5% may represent those patients with false-negative ASST. However upon reanalyzing the data without the two outlying sera, ASST negative chronic urticaria sera still induced CD203c expression above controls. This finding indicates the presence of other undefined serum factors present in CU sera that can upregulate CD203c.

Example 2

The following example demonstrates that CD203c expression in autoimmune CU patients correlates with basophil histamine release.

Figure 4:
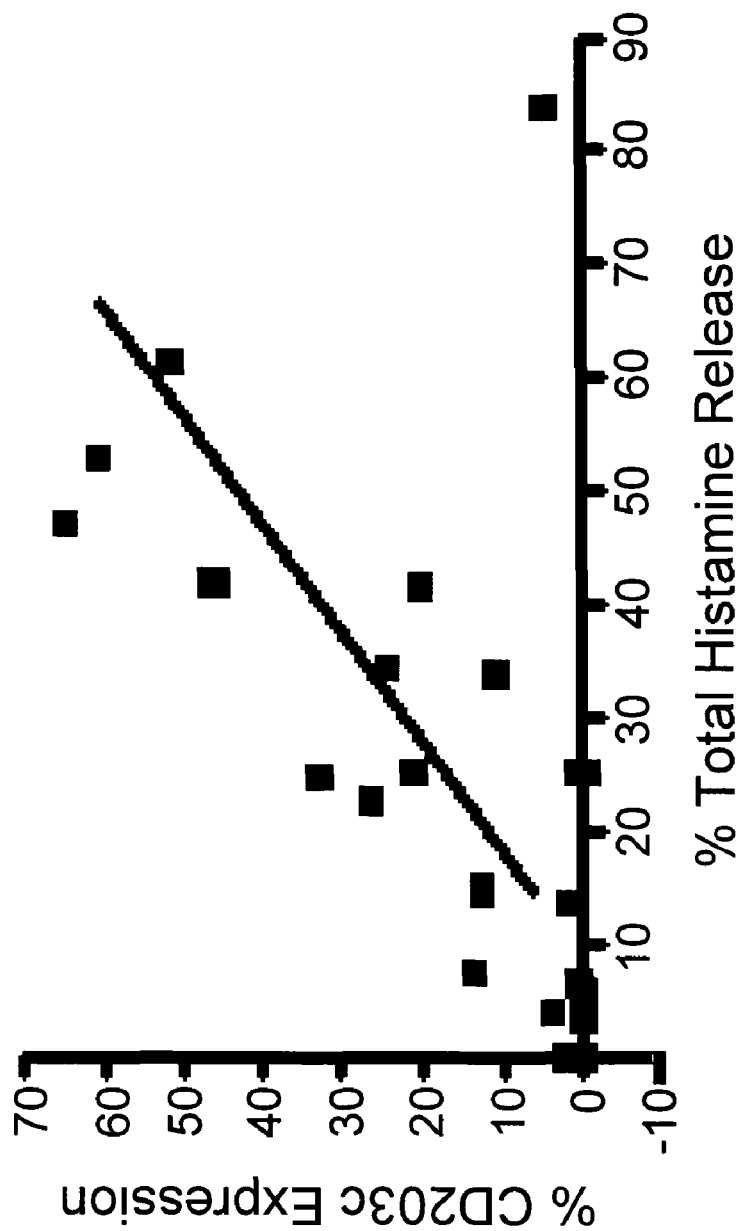
FIG. 4 shows the correlation of CD203c expression with % total histamine release.

BHR was performed in 10 patients with negative ASSTs and in 18 patients with positive ASST. All sera were not analyzed due to insufficient quantity. In patients with negative ASST, 1 of 10 (10%) had a positive BHR, and 4 of 18 (22%) of patients with positive ASSTs had a negative BHR. The percent CD203c expression correlated with the percent histamine release (R=0.6, p=0.001) (FIG. 4). The sensitivity, specificity, positive predictive value and negative predictive value were calculated using the BHR assay as the gold standard to identify functional antibodies to the FcεRIα receptor, and using >5% CD203c expression as the cut-off value for a positive test. Using these criteria, CD203c expression demonstrated a sensitivity of 77%, specificity of 82%, a positive predictive value of 83% and a negative predictive value of 75%.

Example 3

The following example demonstrates a correlation between ASST and CD203c expression.

Figure 5:
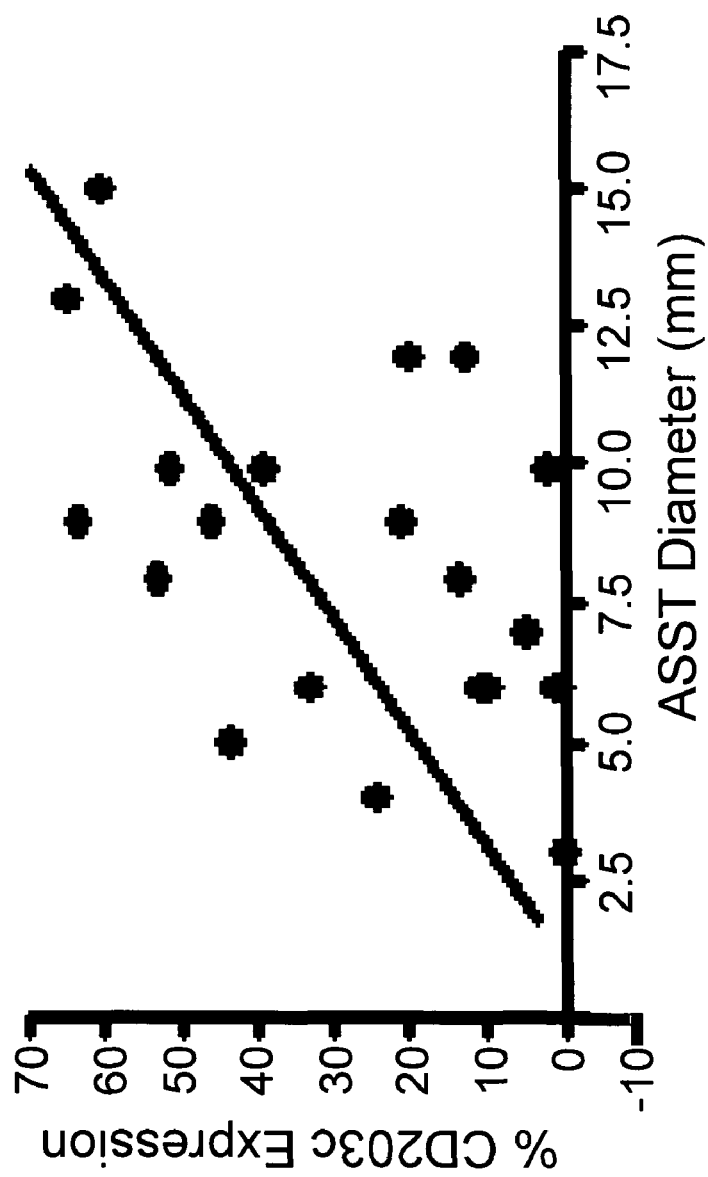
FIG. 5 shows the correlation of percent CD203c expression and ASST mean wheal diameter.

The mean diameter of the serum autologous skin test was compared to percent CD203c expression. Results demonstrated a significant correlation between the size of the ASST and CD203c expression (R=0.5, p=0.02) (FIG. 5).

Example 4

The following example demonstrates that the mechanism of expression of CD203c in CU patients is mediated by IgG.

In order to determine if the mechanism of CD203c expression was mediated by an IgG antibody, 3 selected sera that induced basophil CD203c expression were depleted of IgG using a protein G Sepharose. The mean percent CD203c expression prior to IgG depletion was 30%±9%. The mean percent CD203c expression post IgG depletion was 5%±1%, indicating that in these sera CD203c expression may be triggered by an IgG antibody to FcεRIα. There was no change from pre and post IgG depletion with two control sera 0.2±0.4 (pre) and −0.1±0.02 (post) (p=0.5).

REFERENCES

1. Kaplan A P. Chronic urticaria: pathogenesis and treatment. *J Allergy Clin Immunol,* 2004; 114:465-474.
2. Fiebiger E, Hammerschmid F, Stingle G, Maurer D. Anti-FcepsilonRI alpha autoantibodies in autoimmune-mediated disorders. Identification of a structure-function relationship. *J Clin Invest* 1998; 101:243-251.
3. Sabroe R A, Grattan C E, Francis D M, Barr R M, Kobza Black, A., and Greaves M W. The autologous serum skin test: a screening test for autoantibodies in chronic idiopathic urticaria. *Br J of Dermatol* 1999; 140:446-452.
4. Wedi B, Novacovic V, Koerner M, Kapp A. Chronic urticaria serum induces histamine release, leukotriene production, and basophil CD63 surface expression-inhibitory effects of anti-inflammatory drugs. *J Allergy Clin Immunol* 2000; 105:552-60.
5. Gyimsi E, Sipka S., Danko, K., Kiss E. Hidvegi, B., Gal, M, Hunyadi, J, Irinyi, B, Szegedi, A. Basophil CD63 expression assay on highly sensitized atopic donor leucocytes—a useful method in chronic urticaria. *Br J Dermatol* 2004; 151:388-396.
6. Knol E F, Mul F P J, Jansen H, Calafat J, Roos D. Monitoring human basophil activation via CD63 monoclonal antibody 435. *J Allergy Clin. Immunol* 1991; 88:328-38.
7. Ebo D G, Hagendorens M M, Bridts C H, Schuerwegh A J, De Clerck L S, Stevens W J. In vitro allergy diagnosis: should we follow the flow? *Clin Exp Allergy* 2004; 34:332-339.
8. Buhring H J, Streble A, Valent, P. The basophil-specific ectoenzyme E-NPP3 (CD203c) as a marker for cell activation and allergy diagnosis. *Int Arch Allergy Immunol* 2004; 133:317-29.
9. Boumiza R, Monneret G, Forissier M F, Savoye J, Gutowski M C, Powell W S, Bienveu J. Marked improvement of the basophil activation test by detecting CD203c instead of CD63. *Clin Exp Allergy* 2002; 33:259-65.
10. Binder M, Fierlbeck G, King T, Valent P, Burhing H J. Individual hymenoptera venom compounds induce upregulation of the basophil activation marker ectonucleotide pyrophosphatase/phosphodiesterase 3 (CD203c) in sensitized patients. *Int Arch Allergy Immunol* 2002; 129:160-8.
11. Hauswirth A W, Natter S, Ghannadan M, Majlesi Y, Schernthaner G H, Sperr W R, Buhring H J, Valenta R, Valent P. Recombinant allergens promote expression of CD203c on basophils in sensitized individuals. *J Allergy Clin Immunol* 2002; 127:299-307.
12. Vasgar K, Vonakis, B M, Viksman, A, Gibbons S., Jr. Saini, S. Evidence of in vivo basophil activation in chronic idiopathic urticaria. *J Allergy Clin Immunol* 2003; 113: S257.
13. Ferrer M, Nakazawa K, Kaplan A. Complement dependence of histamine release in chronic urticaria. *J Allergy Clin Immunol* 1999; 104:169-72.
14. Burhing H J, Seiffert M, Giesert C, Marxer A, Valent P, Kanz L, Sano K. The basophil activation marker defined by antibody 97A6 is identical with ecto-nucleotide pyrophosphatase/phosphodiesterase 3 (E-NPP3; CD203c). *Blood* 2001; 97:3303-3305.
15. Monneret G, Boumiza R, Gravel S, Cossette C, Bienvenu J, Rokach J, Powell W S. Effects of prostaglandin D(2) and 5-lipoxygenase products on the expression of CD203c and CD11b by basophils. *J Pharmacol Exp Ther.* 2005; 312:627-34.
16. Hennersdorf F, Florian S, Jakob A, Baumgartner K, Sonneck K, Nordheim A, Biedermann T, Valent P, Buhring H J. Identification of CD13, CD107a, and CD164 as novel basophil-activation markers and dissection of two response patterns in time kinetics of IgE-dependent upregulation. *Cell Res.* 2005; 15:325-35.

Each reference cited herein is incorporated herein by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to diagnose autoimmune chronic urticaria, comprising:

a) contacting cells with a test biological sample from an individual being diagnosed for autoimmune chronic urticaria, wherein the cells are capable of expressing CD203c and FcεRIα, and upregulate the expression of CD203c upon stimulation of the FcεRIα, and wherein the cells are provided as present in a whole blood sample from a donor or as present in peripheral blood cells from a donor; and b) detecting expression of CD203c on the cells, wherein statistically significant upregulation of CD203c on the cells in the presence of the test biological sample, as compared to CD203c expression on the cells in the absence of contact with the biological sample, or as compared to CD203c expression on the cells when contacted with a negative control sample from an individual who does not have autoimmune chronic urticaria, indicates that the individual has autoimmune chronic urticaria, wherein the upregulation of CD203c occurs due to stimulation of FcεRIα by functional anti-FcεRIα autoantibodies present in the test biological sample, and wherein the test biological sample is a fluid sample.

2. The method of claim 1, wherein the test biological sample is serum or whole blood from the individual.

3. The method of claim 1, wherein the donor does not have autoimmune chronic urticaria.

4. The method of claim 1, wherein the cells have been selected as having high upregulation of CD203c expression after stimulation with a granulocyte activating agent and/or after stimulation of FcεRIα on the cells, as compared to cells from a population of normal individuals that do not have autoimmune chronic urticaria.

5. The method of claim 1, wherein the donor is a non-atopic donor.

6. The method of claim 1, wherein the cells are not cultured with interleukin-3 prior to the step of contacting.

7. The method of claim 1, wherein the cells are selected from the group consisting of: basophils and mast cells.

8. The method of claim 1, wherein the step of detecting is performed by flow cytometry.

9. The method of claim 1, wherein the step of detecting is performed using a CD203c antibody or antigen-binding fragment thereof.

10. The method of claim 9, wherein the antibody is a monoclonal antibody.

11. The method of claim 1, wherein the cells express CD63, and wherein the method further comprises detecting CD63 expression on the cells, wherein increased expression of CD63 in the presence of the test biological sample, as compared to CD63 expression on the cells in the absence of contact with the biological sample, or as compared to CD63 expression on the cells when contacted with a negative control sample from an individual who does not have autoimmune chronic urticaria, further indicates that the individual has autoimmune chronic urticaria.

12. The method of claim 1, further comprising testing the individual by histamine release assay, wherein a positive histamine release assay further indicates that the individual has autoimmune chronic urticaria.

13. The method of claim 1, further comprising testing the individual by autologous serum skin testing (ASST), wherein a positive ASST test further indicates that the individual has autoimmune chronic urticaria.

* * * * *